United States Patent [19]

Cohen et al.

[11] Patent Number: 5,744,482
[45] Date of Patent: Apr. 28, 1998

[54] SEROTONIN AGONIST IN COMBINATION WITH A TACHYKININ RECEPTOR ANTAGONIST IN THE TREATMENT OR PREVENTION OF MIGRAINE

[75] Inventors: Marlene L. Cohen, Carmel; Kirk W. Johnson, Indianapolis; Lee A. Phebus, Fountaintown, all of Ind.

[73] Assignee: Eli Lilly and Company, Indianapolis, Ind.

[21] Appl. No.: 318,391

[22] Filed: Oct. 5, 1994

[51] Int. Cl.$^6$ ...................... A61K 31/405; A61K 31/445
[52] U.S. Cl. ............................................. 514/316; 514/415
[58] Field of Search ...................................... 514/316, 415

[56] References Cited

PUBLICATIONS

Shepheard et al., Br. J. Pharm., 108(1) 11–12 (1993).
Oliver et al., Arzneim.-Forsch./Drug Res., 44(II) 925–928, Aug. 1994.

*Primary Examiner*—Phyllis G. Spivack
*Attorney, Agent, or Firm*—Paul J. Gaylo; David E. Boone

[57] ABSTRACT

Methods for the treatment or prevention of migraines comprising administering to a mammal in need thereof a combination of a tachykinin receptor antagonist and a serotonin agonist are disclosed. The administration may be concurrent or sequential, with either of the two activities being administered first.

5 Claims, 1 Drawing Sheet

FIG. 1

SEROTONIN AGONIST IN COMBINATION WITH A TACHYKININ RECEPTOR ANTAGONIST IN THE TREATMENT OR PREVENTION OF MIGRAINE

BACKGROUND OF THE INVENTION

Migraine headaches are a debilitating condition in which some 53 million persons per year suffer acute pain. In many ways headaches are the cranial equivalent of pain from other visceral organs. As such, headaches may reflect an underlying disturbance in organ function.

The first major treatise on the subject of migraines was published by E. Liveing in 1873, in which he associated the phenomenom with epileptiform activity, or "nerve storms". E. Liveing, *London: Churchill*, (1873). In 1938 Graham and Wolff demonstrated that the administration of ergotamine reduced the amplitude of pulsation in the superficial temporal arteries of patients with headache, and this was often, but not always, accompanied by the alleviation of pain. J. R. Graham and H. G. Wolff, *Archives in Neurology*, 39: 737–763 (1938). This vascular hypothesis proposed that migraine headaches were caused by vasodilation of extracranial blood vessels and that ergot-induced vasoconstriction accounted for its relief. Id. the past ten years it has become clear that meningeal blood vessels possess anatomical and physiological properties shared by other tissues that can be the source of pain. For example, neuropeptide-containing unmyelinated C fibers originating from the trigeminal ganglion innervate meningeal blood vessels. T. P. O'Connor and D. van der Kooy, *Journal of Neurosciences*, 6: 2200–2208 (1986). Trigeminovascular fibers terminate, in part, within the trigeminal nucleus caudilis. Activation of trigeminovascular fibers triggers neuronal responses within brain regions associated previously with the transmission of nociceptive information. A. Strassman, et al., *Brain Research*, 379: 242–250 (1986).

It has become increasingly clear that modern experimental results do not support the enduring concepts of Wolff and his disciples that suggested a simple relationship between vasodilation and pain, and vasoconstriction and relief. Instead, the evidence favors a neurogenic mechanism of drug action based on blockade of neural transmission and neurogenic inflammation.

Since the discovery of serotonin (5-hydroxytryptamine, 5-HT) over four decades ago, the cumulative results of many diverse studies have indicated that serotonin plays a significant role in the functioning of the mammalian body, both in the central nervous system and in peripheral systems as well. Morphological studies of the central nervous system have shown that serotonergic neurons, which originate in the brain stem, form a very diffuse system that projects to most areas of the brain and spinal cord. R. A. O'Brien, *Serotonin in Mental Abnormalities*, 1: 41 (1978); H. W. M. Steinbusch, *HANDBOOK OF CHEMICAL NEUROANATOMY*, Volume 3, Part II, 68 (1984); N. E. Anden, et al., *Acta Physiologica Scandinavia*, 67: 313 (1966). These studies have been complemented by biochemical evidence that indicates large concentrations of 5-HT exist in the brain and spinal cord. H. W. M. Steinbusch, supra.

With such a diffuse system, it is not surprising that 5-HT has been implicated as being involved in the expression of a number of behaviors, physiological responses, and diseases which originate in the central nervous system. These include such diverse areas as sleeping, eating, perceiving pain, controlling body temperature, controlling blood pressure, depression, schizophrenia, and other bodily states. R. W. Fuller, BIOLOGY OF SEROTONERGIC TRANSMISSION, 221 (1982); D. J. Boullin, SEROTONIN IN MENTAL ABNORMALITIES 1: 316 (1978); J. Barchas, et al., *Serotonin and Behavior*, (1973).

Serotonin plays an important role in peripheral systems as well. For example, approximately 90% of the body's serotonin is synthesized in the gastrointestinal system, and serotonin has been found to mediate a variety of contractile, secretory, and electrophysiologic effects in this system. Seroconin may be taken up by the platelets and, upon platelet aggregation, be released such that the cardiovascular system provides another example of a peripheral network that is very sensitive to serotonin. Given the broad distribution of serotonin within the body, it is understandable that tremendous interest in drugs that affect serotonergic systems exists. In particular, receptor-specific agonists and antagonists are of interest for the treatment of a wide range of disorders, including anxiety, depression, hypertension, migraine, compulsive disorders, schizophhrenia, autism, neurodegenerative disorders, such as Alzheimer's disease, Parkinsonism, and Huntington's chorea, and cancer chemotherapy-induced vomiting. M. D. Gershon, et al., THE PERIPHERAL ACTIONS OF 5-HYDROXYTRYPTAMINE, 246 (1989); P. R. Saxena, et al., *Journal of Cardiovascular Pharmacology*, 15:Supplement 7 (1990).

Serotonin produces its effects on cellular physiology by binding to specialized receptors on the cell surface. It is now recognized that multiple types of receptors exist for many neurotransmitters and hormones, including serotonin. The existence of multiple, structurally distinct serotonin receptors has provided the possibility that subtype-selective pharmacologic agents can be produced. The development of such compounds could result in new and increasingly selective therapeutic agents with fewer side effects, since activation of individual receptor subtypes may function to affect specific actions of the different parts of the central and/or peripheral serotonergic systems.

An example of such specificity can be demonstrated by using the vascular system as an example. In certain blood vessels, stimulation of 5-$HT_1$-like receptors on the endothelial cells produces vasodilation while stimulation of 5-$HT_2$ receptors on the smooth muscle cells produces vasoconstriction. Conversely, certain 5$HT_1$-like receptors mediate vasoconstriction.

Currently, the major classes of serotonin receptors (5-$HT_1$, 5-$HT_2$, 5-$HT_3$, 5-$HT_4$, 5-$HT_5$, 5-$HT_6$, and 5-$HT_7$) contain some fourteen to eighteen separate receptors that have been formally classified based on their pharmacological or structural differences. [For an excellent review of the pharmacological effects and clinical implications of the various 5-HT receptor types, see Glennon, et al., *Neuroscience and Behavioral Reviews*, 14: 35 (1990).]

Tachykinins are a family of peptides which share the common amidated carboxy terminal sequence, Phe—Xaa—Gly—Leu—Met—$NH_2$ hereinafter referred to as SEQ ID NO:1. Substance P was the first peptide of this family to be isolated, although its purification and the determination of its primary sequence did not occur until the early 1970's. Substance P has the following amino acid sequence, Arg—Pro—Lys—Pro—Gln—Gln—Phe—Phe—Gly—Leu—Met—$NH_2$ hereinafter referred to as SEQ ID NO:2.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3): 237–243 (1985) for a review of these discoveries. Neurokinin A has the following amino acid sequence, hereinafter referred to as SEQ ID NO:3. The structure of neurokinin B is the amino acid sequence, hereinafter referred to as SEQ ID NO:4.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

Tachykinins play a major role in mediating the sensation and transmission of pain or nociception, especially migraine headaches. see, e.g., S. L. Shepheard, et al., *British Journal of Pharmacology*, 108: 11–20 (1993); S. M. Moussaoui, et al., *European Journal of Pharmacology*, 238: 421–424 (1993); and W. S. Lee, et al., *British Journal of Pharmacology*, 112: 920–924 (1994).

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in European Patent Publication 591, 040 A1, published Apr. 6, 1994; Patent Cooperation Treaty publication Wo 94/01402, published Jan. 20, 1994; Patent Cooperation Treaty publication Wo 94/04494, published Mar. 3, 1994; Patent Cooperation Treaty publication Wo 94/07843, published Apr. 14, 1994; and Patent Cooperation Treaty publication WO 93/01169, published Jan. 21, 1993.

The current treatments of migraine generally involve two classes of compounds. The first, the ergot alkaloids, typified by dihydroergotamine, are thought to act as alpha adrenergic blocking agents with direct stimulating effects on the smooth muscle of peripheral and cranial blood vessels and to produce depression of central vasomotor centers. The second class of compounds, typified by sumatriptan, are thought to act as serotonin agonists specific for the 5-HT$_1$ receptor subtype. The ergot alkaloids also demonstrate some activity as serotonin agonists, though not with the specificity shown by sumatriptan. All of these compounds, however, have serious adverse effects which require supervised administration at efficacious doses. PHYSICIAN'S DESK REFERENCE, (48th ed., 1994).

Because of the current dissatisfaction of the currently marketed treatments for migraine within the affected population, there exists a need for a more efficacious and safe treatment.

SUMMARY OF THE INVENTION

This invention provides methods for the treatment or prevention of migraines in a mammal which comprise administering to a mammal in need thereof an effective amount of a composition having both tachykinin receptor antagonist activity and serotonin agonist activity.

This invention further provides methods for the treatment or prevention of migraines in a mammal which comprise the sequential administration to a mammal in need thereof a composition having serotonin agonist activity followed by the administration of a composition having tachykinin receptor antagonist activity.

This invention also provides methods for the treatment or prevention of migraines in a mammal which comprise the sequential administration to a mammal in need thereof a composition having tachykinin receptor antagonist activity followed by the administration of a composition having serotonin agonist activity.

DESCRIPTION OF THE FIGURE

FIG. 1 depicts the result of a typical experiment in which the extravasation ratio of the stimulated dura to the unstimulated dura is plotted against the dosage of the test compound. The closed circles (●) abutting the Y axis demonstrate the effect seen when only saline is added. The open circles (○) represent the administration of (R)-2-[N-(2-((4-cyclohexyl)piperazin-1-yl)acetyl)amino]-3-(1H-indol-3-yl)-1-[N-(2-methoxybenzyl)acetylamino]propane alone. The closed squares (■) represent the dose response curve generated with sumatriptan alone. The closed triangles (▲) represent the dose response curve generated when varying dosages of (R)-2-[N-(2-((4-cyclohexyl)piperazin-1-yl)acetyl)amino]-3-(1H-indol-3-yl)-1-[N-(2methoxybenzyl)acetylamino] propane are administered in conjunction with 1.2 ng/kg of sumatriptan.

DETAILED DESCRIPTION AND PREFERRED EMBODIMENTS

The terms and abbreviations used in the instant preparations and examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "L" means liter or liters; "M" refers to molar or molarity; "MS" refers to mass spectrometry; "IR" refers to infrared spectroscopy; and "NMR" refers to nuclear magnetic resonance spectroscopy.

Many serotonin binding receptors have been identified. These receptors are generally grouped into seven classes on the basis of their structure and the pharmacology of the receptor as determined by the binding efficiency and drug-related characteristics of numerous serotonin receptor-binding compounds. In some of the groups several subtypes have been identified. [For a relatively recent review of 5-hydroxytryptamine receptors, see, E. Zifa and G. Fillion, *Pharamcological Reviews*, 44: 401–453 (1992); D. Hoyer, et al., *Pharamcological Reviews*, 46: 157–203 (1994).] Table I, infra, lists the seven classes of serotonin receptors as well as several known subtypes. This table also provides the physiological distribution of these receptors as well as biological responses mediated by the receptor class or subtype, if any such response is known. This table is derived from D. Hoyer, et al., "VII. International Union of Pharmacology Classification of Receptors for 5-Hydroxytryptamine (Serotonin)", *Pharamcological Reviews*, 46: 157–203 (1994), a publication of the Serotonin Club Receptor Nomenclature Committee of the IUPHAR Committee for Receptor Nomenclature.

TABLE I

| Receptor Type | Subtype | Location | Response |
|---|---|---|---|
| 5-HT$_1$ | 5-HT$_{1A}$ | Neuronal, mainly in CNS | Neuronal hyperpolarisation, hypotension |
| | 5-HT$_{1B}$ | CNS and some peripheral nerves | Inhibition of neurotransmitter release |
| | 5-HT$_{1D}$ | Mainly CNS | Inhibition of neurotransmitter release |
| | 5-HT$_{1E}$ | Only CNS | Inhibition of adenylyl cyclase |
| | 5-HT$_{1F}$ | Mainly CNS | Inhibition of adenylyl cyclase |
| | 5-HT$_1$-like | Intracranial vasculature | Smooth muscle contraction |
| 5-HT$_2$ | 5-HT$_{2A}$ | Vascular smooth muscle, platelets, lung, CNS, gastrointestinal tract | Vasoconstriction, platelet aggregation, bronchoconstriction |
| | 5-HT$_{2B}$ | Mainly peripheral, some CNS | Rat stomach fundic muscle contraction |
| | 5-HT$_{2C}$ | CNS (high density in choroid plexus) | upregulates phosphoinositide turnover |
| 5-HT$_3$ | | Peripheral and central neurones | Depolarization |
| 5-HT$_4$ | | Gastrointestinal tract, CNS, heart, urinary bladder | Activation of acetyl chloline release in gut, tachycardia, upregulates cAMP in CNS neurones |
| 5-HT$_5$ | 5-HT$_{5A}$ | CNS | Not known |
| | 5-HT$_{5B}$ | CNS | Not known |
| 5-HT$_6$ | | CNS | Activation of adenylyl cyclase |
| 5-HT$_7$ | | CNS | Activation of adenylyl cyclase |

The Hoyer, et al., reference describes for each class or subtype one or more compounds which have efficacy as antagonists or agonists for the receptor.

The 5-HT$_1$ family includes subtypes which can be grouped together based on the absence of introns in the cloned genes, a common G-coupled protein transduction system (inhibition of adenylate cyclase), and similar operational characteristics. The 5-HT$_1$ family of inhibitory receptors includes subtypes A, B, D, E, and F. The 5-HT$_1$ G protein-linked receptors general inhibit the production of cyclic adenosine monophosphate (cAMP), while the 5-HT$_2$ G protein linked receptors stimulate phosphoinosytol hydrolysis.

The 5-HT$_{1A}$ receptor was the first cloned human serotonin receptor. Activated 5-HT$_{1A}$ receptors expressed in HeLa cells inhibit forskolin-stimulated adenylate cyclase activity. The 5-HT$_{1D}$ receptor was originally identified in bovine brain membrane by Heuring and Peroutka. R. E. Heuring and S. J. Peroutka, *Journal of Neuroscience*, 7: 894–903 (1937). The 5-HT$_{1D}$ receptors are the most common 5-HT receptor subtype in the human brain and may be identical to the 5-HT$_{1-like}$ receptor in the cranial vasculature. S. D. Silberstein, *Headache*, 34: 408–417 (1994). Sumatriptan and the ergot alkaloids have high affinity for both the human 5-HT$_{1D}$ and the 5-HT$_{1B}$ receptors. Id.

The 5-HT$_{1F}$ subtype of receptor has low affinity for 5-carboxamidotryptamine (5-CT) unlike the other 5-HT receptors, except for the 5-HT$_{1E}$ subtype. Unlike the 5-HT$_{1E}$ receptors, however, the 5-HT$_{1F}$ receptors do show affinity for sumatriptan.

During a migraine attack, platelet 5-HT decreases, urinary 5-HT increases in some patients, and 5-hydroxyindolacetic acid (5-HIAA), a major metabolite of 5-HT, may increase. Id. Some believe a plasma 5-HT releasing factor may appear. Headaches which may be similar to migraine can be triggered by 5-HT releasing agents such as fenfluramine or reserpine and exacerbated by selective inhibition of 5-HT reuptake by drugs such as zimelodine.

Because of the role of serotonin receptors in the mediation of migraine the use of compounds which interact with these receptors should prove efficacious. Preferred compounds are those compounds which interact with a subset of the serotonin receptors.

The biological efficacy of a compound believed to be effective as a serotonin agonist may be confirmed by first employing an initial screening assay which rapidly and accurately measures the binding of the test compound to one or more serotonin receptors. Once the binding of the test compound to one or more serotonin receptors is established, the in vivo activity of the test compound on the receptor is established. Assays useful for evaluating serotonin agonists are well known in the art. See, e.g., E. Zifa and G. Fillion, supra; D. Hoyer, et al., supra, and the references cited therein.

Serotonin Receptor Binding Activity

Binding to the 5-HT$_{1F}$ receptor.

The ability of a compound to bind to a serotonin receptor was measured using standard procedures. For example, the ability of a compound to bind to the 5-HT$_{1F}$ receptor subtype was performed essentially as described in N. Adham, et al., *Proceedings of the National Academy of Sciences (USA)*, 90: 403–412 (1993).

The cloned 5-HT$_{1F}$ receptor was expressed in stably transfected LM(tk$^-$) cells. Membrane preparations were made by growing these transfected cell lines to confluency. The cells were washed twice with phosphate-buffered saline, scraped into 5 ml of ice-cold phosphate-buffered saline, and centrifuged at 200×g for about five minutes at 4° C. The pellet was resuspended in 2.5 ml of cold Tris buffer (20 mM Tris.HCl, pH 7.4 at 23° C., 5 mM EDTA) and homogenized. The lysate was centrifuged at 200×g for about five minutes at 4° C. to pellet large fragments. The supernatant was then centrifuged at 40,000×g for about 20 minutes at 4° C. The membranes were washed once in the homogenization buffer and resuspended in 25 mM glycylclycine buffer, pH 7.6 at 23° C.

Radioligand binding studies were performed using [$^3$H] 5-HT (20–30 Ci/mmol). Competition experiments were done by using various concentrations of drug and 4.5–5.5 nM [$^3$H]5-HT. Nonspecific binding was defined by 10 μM 5-HT. Binding data were analyzed by nonlinear-regression analysis. IC$_{50}$ values were converted to Ki values using the Cheng-Prusoff equation.

For comparison purposes, the binding affinities of compounds for various serotonin receptors may be determined essentially as described above except that different cloned receptors are employed in place of the 5-HT$_{1F}$ receptor clone employed therein.

Serotonin Agonist Activity

Adenylate Cyclase Activity.

Adenylate cyclase activity was determined in initial experiments in LM(tk-) cells, using standard techniques. See, e.g., N. Adham, et al., supra.; R. L. Weinshank, et al., *Proceedings of the National Academy of Sciences (USA)*, 89: 3630–3634 (1992), and the references cited therein.

Intracellular levels of cAMP were measured using the clonally derived cell line described above. Cells were pre-incubated for about 20 minutes at 37° C. in 5% carbon dioxide, in Dulbecco's modified Eagle's medium containing 10 mM HEPES, 5 mM theophylline, and 10 µm pargyline. Varying concentrations of the test compounds were added to ths medium to determine inhibition of forskolin-stimulated adenylate cyclase.

Some compounds that bind serotonin receptors show no receptor selectivity, i.e. they bind different receptor subtypes with comparable affinity. One example of such a non-selective serotonin receptor binding compound is dihydroergotamine, a compound having the structure and the chemical name, 9,10-dihydro-12'-hydroxy-2'-methyl-5'-(phenylmethyl)ergotaman-3',6',18'-trione. This compound is commercially available [as the mesylate salt] or may be prepared as described in Stoll and Hofmann, *Helv. Chimica Acta*, 26: 2070 (1943).

A compound having a high affinity for one (or a few) receptor subtype and low affinity for other receptor subtypes using studies analogous to the binding assays supra, is considered to be subtype-selective. Such compounds are especially preferred in the methods of the present invention.

One example of such a compound is sumatriptan, a compound having the structure and the chemical name, 3-[2-(dimethylamino)ethyl]-N-methyl-1H-indole-5-methanesulfonamide. This compound is commercially available or may be prepared as described in U.S. Pat. No. 5,037,845, issued Aug. 6, 1991, which is herein incorporated by reference. Sumatriptan is selective for the 5-HT$_1$ receptor subtypes.

An additional serotonin agonist which is specific for the 5-HT$_1$ class of receptors is a compound of the structure having the designation 311C90 and the chemical name (S)-4-[[3-[2-(dimethylamino)ethyl]-1H-indol-5-yl]methyl]-2-oxazolidinone. This compound may be synthesized as described in Patent Cooperation Treaty Publication WO 91/18897, published Dec. 12, 1991. Unlike sumatriptan, 311C90 is believed capable of crossing the blood-brain barrier. Scrip, Sep. 7, 1994.

Some additional classical serotonin agonists which are frequently employed are:

(a) Rauwolscine—a compound of the formula having the chemical name 17α-hydroxy-20α-yohimban-16β-carboxylic acid methyl ester. This compound, also known as α-yohimbine, can be prepared as described in Töke, et al., *Journal of Organic Chemistry*, 38: 2496 (1973) or can be purchased commercially from many sources.

(b) Yohimbine—a compound also known as allo-yohimbine having the formula with the chemical name 17-hydroxyyohimban-16-carboxylic acid methyl ester. This compound, which is available from commercial sources, can also be synthesized as described in Töke, et al., supra.

(c) α-Methyl-5-hydroxytryptamine—a compound of the formula having the chemical name 3-(2-aminopropyl)-1H-indol-5-ol, which is available from commercial sources.

(d) 1-(1-Naphthyl)piperazine—a compound of the formula which is described in U.S. Pat. No. 4,520,024, issued May 28, 1985, which is herein incorporated by reference.

(e) metoclopramide—a compound of the formula having the chemical name 4-amino-5-chloro-N-[(2-diethylamino)ethyl]-2-methoxybenzamide, which is described in U.S. Pat. No. 3,177,252, which is herein incorporated by reference.

The above groups of compounds are only illustrative of the serotonin receptor agonists which are currently under development or are frequently employed in serotonin receptor studies. This listing of groups of compounds is not meant to be comprehensive, the methods of the present invention may employ any serotonin receptor agonist and is not limited to any particular class of compound.

Sumatriptan and the ergot alkaloids have serious disadvantages at the dosages considered efficacious for treatment of migraine. Both types of compounds are administered as injections, the ergot alkaloids are usually administered as an intramuscular injection, whereas sumatriptan is usually administered as a subcutaneous injection. PHYSICIAN'S DESK REFERENCE, supra. Intravenous injection of either may result in coronary vasospasm. Id. Both types of compounds are also contraindicated for patients suffering from uncontrolled hypertension due to the vasoconstrictive properties. Id. Patients taking either type of compound frequently complain of nausea, chest tightness, and other adverse events. Id., See also, Scrip, No. 1952, Aug. 26, 1994, at page 15.

The methods of the present invention, in addition to the serotonin agonists, examples of which are described above, also employ various tachykinin receptors. In recent publications many different groups of non-peptidyl tachykinin receptor antagonists have been described.

Patent Cooperation Treaty publication WO 94/01402, published Jan. 20, 1994, describes a series of compounds best typified by the following compound.

European Patent Publication 591,040 A1, published Apr. 6, 1994 describes a series of compounds typified by the following compound:

where A$^\ominus$ is a pharmaceutically acceptable anion.

Patent Cooperation Treaty publication WO 94/04494, published Mar. 3, 1994, describes a series of compounds typified by the following compound.

Patent Cooperation Treaty publication WO 93/01169, published Jan. 21, 1993, describes a series of compounds typified by the following compound.

Another group of tachykinin receptor antagonists is characterized by the compound of the formula:

having the designation (±)-CP 96345. These compounds and their syntheses are described in E. J. Warawa, et al., *Journal of Medicinal Chemistry*, 18: 357 (1975).

Yet another group of tachykinin receptor antagonists is characterized by the compound of the formula:

having the designation RP 67580. These compounds and their syntheses are described in C. Garret, et al., *Proceedings of the National Academy of Sciences (USA)*, 88: 10208–10211 (1991) and the references cited therein.

Patent Cooperation Treaty publication WO 94/07843 describes a series of cyclohexylamine derivatives typified by the following compound which are useful as tachykinin receptor antagonists.

Another group of compounds useful as tachykinin receptor antagonists is typified by the following compound.

The synthesis of these compounds is described in co-pending U.S. patent application Ser. No. 08/235401, filed Apr. 29, 1994.

The above groups of compounds are only illustrative of the tachykinin receptor antagonists which are currently under development. This listing of groups of compounds is not meant to be comprehensive, the methods of the present invention may employ any tachykinin receptor antagonist and is not limited to any particular class of compound.

A most preferred class of tachykinin receptor antagonists are those compounds of the following structure where $R^1$ and $R^2$ are independently selected from the group consisting of hydrogen, methyl, methoxy, chloro, and trifluoromethyl, with the proviso that no more than one of $R^1$ and $R^2$ can be hydrogen; and Y is N—$R^a$, or CH—N$R^b R^c$, where $R^a$, $R^b$, and $R^c$ are independently selected from the group consisting of hydrogen and $C_1$–$C_6$ alkyl;

or a pharmaceutically acceptable salt or solvate thereof. The synthesis of these compounds is described in co-pending U.S. patent application Ser. No. 08/153,847, filed Nov. 17, 1993. The syntheses of two typical compounds from this class are detailed infra.

Synthesis of (R)-2-[N-(2-((4-cyclohexyl)piperazin-1-yl)acetyl)amino]-3-(1H-indol-3-yl)-1-[N-(2-methoxybenzyl)acetylamino]propane (a) Preparation of (R)-3-(1H-indol-3-yl)-2-(N-triphenylmethylamino)propanoic acid [N-trityltryptophan]

Tritylation

Chlorotrimethylsilane (70.0 ml, 0.527 mol) was added at a moderate rate to a stirred slurry of D-tryptophan (100.0 g, 0.490 mol) in anhydrous methylene chloride (800 ml) under a nitrogen atmosphere. This mixture was continuously stirred for 4.25 hours. Triethylamine (147.0 ml, 1.055 mol) was added, followed by the addition of a solution of triphenylmethyl chloride (147.0 g, 0.552 mol) in methylene chloride (400 ml) using an addition funnel. The mixture was stirred at room temperature, under a nitrogen atmosphere for at least 20 hours. The reaction was quenched by the addition of methanol (500 ml).

The solution was concentrated on a rotary evaporator to near dryness and the mixture was redissolved in methylene chloride and ethyl acetate. An aqueous workup involving a 5% citric acid solution (2×) and brine (2×) was then performed. The organic layer was dried over anhydrous sodium sulfate, filtered, and concentrated to dryness on a rotary evaporator. The solid was dissolved in hot diethyl ether followed by the addition of hexanes to promote crystallization. By this process 173.6 g (0.389 mol) of analytically pure (R)-3-(1H-indol-3-yl)-2-(N-triphenylmethylamino) propanoic acid was isolated as a white solid in two crops giving a total of 79% yield. FDMS 446 (M+).

$^{1}$H NMR (DMSO-$d_6$) δ 2.70 (m, 1H), 2.83 (m, 2H), 3.35 (m, 1H), 6.92–7.20 (m, 12H), 7.30–7.41 (m, 8H), 10.83 (S, 1H), 11.73 (br s, 1H).

Analysis for $C_{30}H_{26}N_2O_2$:

Theory: C, 80.69; H, 5.87; N, 6.27.
Found: C, 80.47; H, 5.92; N, 6.10.

(b) Preparation of (R)-3-(1H-indol-3-yl)-N-(2-methoxybenzyl)-2-(N-triphenylmethylamino)propanamide Coupling To a stirred solution of (R)-3-(1H-indol-3-yl)-2-(N-triphenylmethylamino)propanoic acid (179.8 g, 0.403 mol), 2-methoxybenzylamine (56.0 ml, 0.429 mol), and hydroxybenzotriazole hydrate (57.97 g, 0.429 mol) in anhydrous tetrahydrofuran (1.7 L) and anhydrous N,N-dimethylformamide (500 ml) under a nitrogen atmosphere at 0° C., were added triethylamine (60.0 ml, 0.430 mol) and 1-(3-dimethylaminopropyl)-3-ethoxycarbodiimide hydrochloride (82.25 g, 0.429 mol). The mixture was allowed to warm to room temperature under a nitrogen atmosphere for at least 20 hours. The mixture was concentrated on a rotary evaporator and then redissolved in methylene chloride and an aqueous work-up of 5% citric acid solution (2×), saturated sodium bicarbonate solution (2×), and brine (2×) was performed. The organic layer was dried over anhydrous sodium sulfate and concentrated to dryness on a rotary evaporator. The desired product was then recrystallized from hot ethyl acetate to yield 215.8 g (0.381 mol, 95%) of analytically pure material. FDMS 565 (M+).

$^{1}$H NMR (CDCl$_3$) δ 2.19 (dd, J=6.4 Hz, Δv=14.4 Hz, 1H), 2.64 (d, J=6.5 Hz, 1H), 3.19 (dd, J=4.3 Hz, Δv=14.4 Hz, 1H), 3.49 (m, 1H), 3.63 (s, 3H), 3.99 (dd, J=5.4 Hz, Δv=14.2 Hz, 1H), 4.25 (dd, J=7.1 Hz, Δv=14.2 Hz, 1H), 6.64 (d, J=2.1 Hz, 1H), 6.80 (d, J=8.2 Hz, 1H), 6.91 (t, J=7.4 Hz, 1H), 7.06–7.38 (m, 21 H), 7.49 (d, J=7.9 Hz, 1H), 7.75 (s, 1H).

Analysis for $C_{38}H_{35}N_3O_2$:

Theory: C, 80.68; H, 6.24; N, 7.43.
Found: C, 80.65; H, 6.46; N, 7.50.

(c) Preparation of (R)-3-(1H-indol-3-yl)-1-[N-(2-methoxybenzyl)amino]-2-(N-triphenylmethylamino) propane Reduction of Carbonyl RED-AL®, [a 3.4M, solution of sodium bis(2-methoxyethoxy)aluminum hydride in toluene] (535 ml, 1.819 mol), dissolved in anhydrous tetrahydrofuran (400 ml) was slowly added using an addition funnel to a refluxing solution of the acylation product, (R)-3-(1H-indol-3-yl)-N-(2-methoxybenzyl)-2-(N-triphenylmethylamino) propanamide (228.6 g, 0.404 mols) produced supra, in anhydrous tetrahydrofuran (1.0 L) under a nitrogen atmosphere. The reaction mixture became a purple solution. The reaction was quenched after at least 20 hours by the slow addition of excess saturated Rochelle's salt solution (potassium sodium tartrate tetrahydrate). The organic layer was isolated, washed with brine (2×), dried over anhydrous sodium sulfate, filtered, and concentrated to an oil on a rotary evaporator. No further purification was done and the product was used directly in the next step.

(d) Preparation of (R)-3-(1H-indol-3-yl)-1-[N(2-methoxybenzyl)-acetylamino]-2-(N-triphenylmethylamino)propane Acylation of Secondary Amine To a stirring solution of (R)-3-(1H-indol-3-yl)-1-[N-(2-methoxybenzyl)amino]-2-(N-triphenylmethylamino) propane (0.404 mol) in anhydrous tetrahydrofuran (1.2 L) under a nitrogen atmosphere at 0° C. was added triethylamine (66.5 ml, 0.477 mol) and acetic anhydride (45.0 ml, 0.477 mol). After 4 hours, the mixture was concentrated on a rotary evaporator, redissolved in methylene chloride and ethyl acetate, washed with water (2×) and brine (2×), dried over anhydrous sodium sulfate, filtered, and concentrated to a solid on a rotary evaporator. The resulting solid was dissolved in chloroform and loaded onto silica gel 60 (230–400 mesh) and eluted with a 1:1 mixture of ethyl acetate and hexanes. The product was then crystallized from an ethyl acetate/hexanes mixture. The resulting product of (R)-3-(1H-indol-3-yl)-1-[N-(2-methoxybenzyl) acetylamino]-2-(N-triphenylmethylamino)propane was crystallized and isolated over three crops giving 203.97 grams (87% yield) of analytically pure material.

Analysis for $C_{40}H_{39}N_3O_2$:

Theory: C, 80.91; H, 6.62; N, 7.08.
Found: C, 81.00; H, 6.69; N, 6.94.

(e) Preparation of (R)-2-amino-3-(1H-indol-3yl)-1-[N-(2-methoxybenzyl)acetylamino]propane Deprotection Formic acid (9.0 ml, 233.540 mmol) was added to a stirring solution of (R)-3-(1H-indol-3-yl)-1-[N-(2-methoxybenzyl)acetylamino]-2-(N-triphenylmethylamino) propane (14.11 g, 23.763 mmol) in anhydrous methylene chloride under a nitrogen atmosphere at 0° C. After 4 hours, the reaction mixture was concentrated to an oil on a rotary evaporator and redissolved in diethyl ether and 1.0N hydrochloric acid. The aqueous layer was washed twice with diethyl ether and basified with sodium hydroxide to a pH greater than 12. The product was extracted out with methylene chloride (4×). The organic extracts were combined, dried over anhydrous sodium sulfate, filtered, and concentrated on a rotary evaporator to a white foam. The compound (R)-2-amino-3-(1H-indol-3-yl)-1-[N-(2-methoxybenzyl) acetylamino]propane (7.52 g, 21.397 mmols) was isolated giving a 90% yield. No further purification was necessary.

(f) Preparation of (R)-2-amino-3-(1H-indol-3-yl)-1-[N-(2-methoxybenzyl)acetylamino]propane dihydrochloride A stirring solution of (R)-3-(1H-indol-3-yl)-1-[N-(2-methoxybenzyl)acetylamino]-2-(N-triphenylmethylamino) propane in two volumes of methylene chloride was cooled to between −40° C. and −50° C. Anhydrous hydrogen chloride gas was added at such a rate that the temperature of the reaction mixture did not exceed 0° C. The reaction mixture was stirred for 30 minutes to one hour at 0°–10° C.

To this reaction mixture was added two volumes of methyl t-butyl ether and the resulting mixture was allowed to stir for 30 minutes to one hour at 0°–10° C. The resulting crystalline solid was removed by filtration and then washed with methyl t-butyl ether. The reaction product was dried under vacuum at 50° C. (Yield >98%)

Analysis for $C_{21}H_{25}N_3O_2 \cdot 2\,HCl$:

Theory: C, 59.44; H, 6.41; N, 9.90.

Found: C. 60.40; H. 6.60; N. 9.99.

(g) Preparation of 2-((4-cyclohexyl)piperazin-1-yl)acetic acid potassium salt hydrate Cyclohexylpiperazine (10.0 g. 0.059 mol) was added to ten volumes of methylene chloride at room temperature. To this mixture was added sodium hydroxide (36 ml of a 2N solution. 0.072 mol) and tetrabutylammonium bromide (1.3 g. 0.004 mol). After the addition of the sodium hydroxide and tetrabutylammonium bromide, methyl bromoacetate (7.0 ml. 0.073 mol) was added and the reaction mixture was stirred for four to six hours. The progress of the reaction was monitored by gas chromatography.

The organic fraction was separated and the aqueous phase was back-extracted with methylene chloride. The organic phases were combined and washed twice with deionized water, once with saturated sodium bicarbonate solution, and then with brine. The organic phase was dried over magnesium sulfate and the solvents were removed in vacuo to yield methyl 2-((4-cyclohexyl)piperazin-1-yl)acetate as a yellowish oil.

The title compound was prepared by dissolving the methyl 2-((4-cyclohexyl)piperazin-1-yl)acetate (10.0 g. 0.042 mol) in ten volumes of diethyl ether. This solution was cooled to 15° C. and then potassium trimethylsilanoate (5.9 g. 0.044) was added. This mixture was then stirred for four to six hours. The reaction product was removed by filtration, washed twice with five volumes of diethyl ether, then washed twice with five volumes of hexanes, and then dried in a vacuum oven for 12–24 hours at 50° C.

Analysis for $C_{12}H_{21}KN_2O_2 \cdot 1.5\ H_2O$:
Theory: C. 49.63; H. 7.98; N. 9.65.
Found: C. 49.54; H. 7.72; N. 9.11.

(h) Preparation of (R)-2-[N-(2-((4-cyclohexyl)piperazin-1-yl)acetyl)amino]-3-(1H-indol-3-yl)-1-[N-(2-methoxybenzyl)acetylamino]propane The title compound was prepared by first cooling 2-((4-cyclohexyl)piperazin-1-yl)acetic acid potassium salt to a temperature between −8° C. and −15° C. in 5 volumes of anhydrous methylene chloride. To this mixture was added isobutylchloroformate at a rate such that the temperature did not exceed −8° C. The resulting reaction mixture was stirred for about 1 hour, the temperature being maintained between −8° C. and −15° C.

To this mixture was then added (R)-2-amino-3-(1H-indol-3-yl)-1-[N-(2-methoxybenzyl)acetylamino]propane dihydrochloride at such a rate that the temperature did not exceed 0° C. Next added to this mixture was N-methyl morpholine at a rate such that the temperature did not exceed 0° C. This mixture was then stirred for about 1 hour at a temperature between −15° C. and −8° C.

The reaction was quenched by the addition of 5 volumes of water. The organic layer was washed once with a saturated sodium bicarbonate solution. The organic phase was then dried over anhydrous potassium carbonate and filtered to remove the drying agent. To the filtrate was then added 2 equivalents of concentrated hydrochloric acid, followed by 1 volume of isopropyl alcohol. The methylene chloride was then exchanged with isopropyl alcohol under vacuum by distillation.

The final volume of isopropyl alcohol was then concentrated to three volumes by vacuum. The reaction mixture was cooled to 20° C. to 25° C. and the product was allowed to crystallize for at least one hour. The desired product was then recovered by filtration and washed with sufficient isopropyl alcohol to give a colorless filtrate. The crystal cake was then dried under vacuum at 50° C. MS 560 (M+1+).

$^1$H NMR (CDCl$_3$) δ 1.09–1.28 (m, 5H), 1.64 (d, J=10 Hz, 1H) 1.80–1.89 (m, 4H), 2.10 (s, 3H), 2.24–2.52 (m, 9H), 2.90 (s, 2H), 2.95 (d, J=7 Hz, 1H), 3.02 (d, J=7 Hz, 1H), 3.12 (dd, J=5, 14 Hz, 1H), 3.77 (s, 3H), 4.01 (dd, J=10, 14 Hz, 1H), 4.49 (ABq, J=17 Hz, 43 Hz, 2H), 4.56 (m, 1H), 6.79–6.37 (m, 3H), 7.05–7.24 (m, 4H), 7.34–7.41 (m, 2H), 7.67 (d, J=8 Hz, 1H), 3.22 (s, 1H).

Analysis for $C_{33}H_{45}N_5O_3$:
Theory: C. 70.31; H. 3.10; N. 12.51.
Found: C. 70.71; H. 3.21; N. 12.42.

Synthesis of (R)-3-(1H-indol-3-yl)-1-[N-(2-methoxybenzyl) acetylamino]-2-[N-(2-(4-(piperidin-1-yl)piperidin-1-yl) acetyl)amino]propane (a) Preparation of 2-(4-(piperidin-1-yl)piperidin-1-yl)acetic acid, potassium salt 4-(Piperidin-1-yl)piperidine (1.20 kg, 7.13 mol) was added to methylene chloride (12.0 L) under a nitrogen atmosphere. Tetrabutylammonium bromide (0.150 kg, 0.47 mol) and sodium hydroxide (1.7 L of a 5N solution, 8.5 mol) were then added. The reaction mixture was cooled to 10°–15° C. and methyl bromoacetate (1.17 kg, 7.65 mol) was added and the resulting mixture was stirred for a minimum of 16 hours.

Deionized water (1.2 L) was then added to the mixture and the layers separated. The aqueous layer was back-extracted with methylene chloride (2.4 L). The organic fractions were combined and washed with deionized water (3×1.2 L), a saturated sodium bicarbonate solution (1.1 L) and a saturated sodium chloride solution (1.1 L). The organic fraction was then dried over anhydrous magnesium sulfate and concentrated to an oil on a rotary evaporator to yield 1.613 kg (93.5%) of methyl 2-(4-(piperidin-1-yl) piperidin-1-yl)acetate.

A solution of methyl 2-[4-(piperidin-1-yl)piperidin-1-yl] acetate (2.395 kg, 9.96 mol) in methanol (2.4 L) was added to a solution of potassium hydroxide (0.662 kg, 10.0 mol @ 85% purity) in methanol (10.5 L) under a nitrogen atmosphere. The reaction mixture was heated to 45°–50° C. for a minimum of 16 hours.

A solvent exchange from methanol to acetone (15.0 L) was performed on the solution on a rotary evaporator. This solution was slowly cooled to room temperature over 16 hours. The resulting solids were filtered, rinsed with acetone (5.0 L) and then dried to yield 2.471 kg (93.8%) of 2-(4-(piperidin-1-yl)piperidin-1-yl)acetic acid, potassium salt. MS 265 (M$^{+1}$).

(b) Preparation of (R)-3-(1H-indol-3-yl)-1-[N(2-methoxybenzyl)acetylamino]-2-[N-(2-(4-(piperidin-1-yl) piperidin-1-yl)acetyl)amino]propane The title compound was prepared by first admixing (R)-2-amino-3-(1H-indol-3-yl)-1-[N-(2-methoxybenzyl) acetylamino]propane dihydrochloride (50.0 g, 0.118 mol) with 100 ml of methylene chloride under a nitrogen atmosphere.

In a second flask, under a nitrogen atmosphere, 2-(4-(piperidin-1-yl)piperidin-1-yl)acetic acid potassium salt (62.3 g, 0.236 mol) was added to 600 ml of methylene chloride. This mixture was cooled to about −10° C. and stirring was continued. To this mixture isobutylchloroformate (23 ml, 0.177 mol) was added dropwise such that the temperature of the 2-(4-(piperidin-1-yl)piperidin-1-yl)acetic acid potassium salt mixture never rose appreciably.

This reaction mixture was stirred at about −10° C. for about 1.5 hours at which time the (R)-2-amino-3-(1H-indol-3-yl)-1-[N-(2-methoxybenzyl)acetylamino]propane dihydrochloride/methylene chloride mixture prepared supra was slowly added to the 2-(4-(piperidin-1-yl)piperidin-1-yl) acetic acid potassium salt/isobutylchloroformate/methylene chloride solution. The resulting mixture was then stirred for about 1 hour at a temperature between −15° C. and −8° C.

The reaction mixture was removed from the ice bath and allowed to warm to 15°−20° C. and the reaction was quenched by the addition of 200 ml of water. The pH of the solution was adjusted to 2.3–2.7 by the addition of 1N sulfuric acid. The layers were separated and the aqueous layer was washed with 100 ml of methylene chloride.

The organic fractions were combined and washed with water (100 ml). The water wash was back extracted with methylene chloride (50 ml) and combined with the aqueous fraction from above. Methylene chloride (500 ml) was added to the combined aqueous layers and the mixture was stirred at room temperature for 15 minutes as basification with 2N sodium hydroxide to a final pH of 9.8 to 10.2 was achieved.

The organic and aqueous fractions were separated. The aqueous fraction was washed with methylene chloride and the methylene chloride was added to the organic fraction. The organic fraction was then washed with a mixture of saturated sodium bicarbonate solution (100 ml) and water (50 ml). The bicarbonate wash was separated from the organic fraction and back extracted with methylene chloride (50 ml). The back extraction was combined with the methylene chloride fraction and the combined fractions were dried over magnesium sulfate. The magnesium sulfate was removed by filtration and the volatiles were removed by vacuum distillation to yield the title product as a foam. (72.5 g, >98% yield). MS 559($M^{+1}$)

NMR (DMSO-$d_6$ 3:2 mixture of amide rotamers) δ 1.25–1.70 (m, 10H), 1.77–2.00 (m, 2H), 1.95 (s, 3/5.3H), 2.04 (s, 2/5.3H), 2.10–2.97 (m, 9H), 3.10–3.65 (m, 3H), 3.72 (s, 2/5.3H), 3.74 (s, 3/5.3H), 4.26–4.58 (m, 3H), 6.76–7.12 (m, 6H), 7.13–7.35 (m, 2H), 7.42–7.66 (m, 2H), 10.80 (br s, 1H).

Analysis for $C_{33}H_{45}N_5O_3$:
Theory: C, 70.31; H, 3.10; N, 12.51.
Found: C, 70.57; H, 8.05; N, 12.39.

The biological efficacy of a compound believed to be effective as a tachykinin receptor antagonist may be confirmed by employing an initial screening assay which rapidly and accurately measured the binding of the tested compound to known NK-1 and NK-2 receptor sites. Assays useful for evaluating tachykinin receptor antagonists are well known in the art. See, e.g., J. Jukic, et al., *Life Sciences*, 49: 1463–1469 (1991); N. Kucharczyk, et al., *Journal of Medicinal Chemistry*, 36: 1654–1661 (1993); N. Rouissi, et al., *Biochemical and Biophysical Research Communications*, 176: 394–901 (1991).

NK-1 Receptor Binding Assay

Radioreceptor binding assays were performed using a derivative of a previously published protocol. D. G. Payan, et al., *Journal of Immunology*, 133: 3260–3265 (1934). In this assay an aliquot of IM9 cells (1×10$^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized cell line which is readily available to the public. See, e.g., *Annals of the New York Academy of Science*, 190: 221–234 (1972); *Nature (London)*, 251: 443–444 (1974); *Proceedings of the National Academy of Sciences (USA)*, 71: 34–83 (1974). These cells were routinely cultured in RPMI 1640 supplemented with 50 µg/ml gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, were grown in 75 cm$^2$ flasks or roller bottles in minimal essential medium (alpha modification) with 10% fetal bovine serum. The gene sequence of the human NK-2 receptor is given in N. P. Gerard, et al., *Journal of Biological Chemistry*, 265: 20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets were washed once using the above procedure and the final pellets were resuspended in 100–120 ml 50 mM Tris buffer, pH 7.4, and 4 ml aliquots stored frozen at −70° C. The protein concentration of this preparation was 2 mg/ml.

For the receptor binding assay, one 4-ml aliquot of the CHO-hNK-2R membrane preparation was suspended in 40 ml of assay buffer containing 50 mM Tris, pH 7.4, 3 mM manganese chloride, 0.02% bovine serum albumin (BSA) and 4 µg/ml chymostatin. A 200 µl volume of the homogenate (40 µg protein) was used per sample. The radioactive ligand was [$^{125}$I]iodohisticlyl-neurokinin A (New England Nuclear, NEX-252), 2200 Ci/mmol. The ligand was prepared in assay buffer at 20 nCi per 100 µl; the final concentration in the assay was 20 pM. Non-specific binding was determined using 1 µM eledoisin. Ten concentrations of eledoisin from 0.1 to 1000 nM were used for a standard concentration-response curve.

All samples and standards were added to the incubation in 10 µl dimethylsulfoxide (DMSO) for screening (single dose) or in 5 µl DMSO for IC$_{50}$ determinations. The order of additions for incubation was 190 or 195 µl assay buffer, 200 µl homogenate, 10 or 5 µl sample in DMSO, 100 µl radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 ml of cold 50 mM Tris buffer, pH 7.7. The filter circles were then punched into 12×75 mm polystyrene tubes and counted in a gamma counter.

The value of the combination of a serotonin agonist and a tachykinin receptor antagonist in the treatment of migraine may be best described by the following experiment which clearly demonstrates the inhibitory effect of the combination therapy on an animal model predictive of migraine therapies.

Neurogenic Plasma Estravasation in the Dural Layer Induced by Electrical Stimulation Harlan Sprague-Dawley rats (225–325 g) or guinea pigs from Charles River Laboratories (225–325 g) were anesthetized with sodium phenobarbitol (65 mg/kg or 45 mg.kg, respectively, intraperitoneally) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally for rats; 4 mm posteriorly and 3.2 and 5.2 mm laterally for guinea pigs—all coordinates reference to bregma). Pairs of stainless steel stimulating electrodes, insulated except for the tips, were lowered through the holes in both hemispheres to a depth of 9 mm (rats) or 10.5 mm (guinea pigs) from dura.

The femoral vein was exposed and a dose of the test compound was injected intravenously (1 ml/kg). Approximately seven minutes later, a 50 mg/kg dose of Evans Blue, a fluorescent dye, was also injected intravenously. The Evans Blue complexed with proteins in the blood and functioned as a marker for protein extravasation. Exactly ten minutes post-injection of the test compound, the left trigeminal ganglion was stimulated for three minutes at a current intensity of 1.0 mA (5 Hz, 4 msec duration) with a potentiostat/galvanostat.

Fifteen minutes following the stimulation, the animals were killed and exanguinated with 20 ml of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorscence microscope equipped with a grating monochromator and a spectrophotometer was used to quantify the amount of Evans Blue dye in each tissue sample An excitation wavelength of approximately 535 nm was utilized and the emission intensity at 600 nm was determined. The miroscope was equipped with a motorized stage and was interfaced with a personal computer. This facilitated the computer-controlled movement of the stage with fluorescence measurements at 25 points (500 μm steps) on each dural sample. The mean and standard deviation of the measurements were determined by the computer.

The dural extravasation induced by electrical stimulation of the trigeminal ganglion was an ipsilateral effect (i.e. it occurs only on the side of the dura in which the trigeminal ganglion was stimulated). This allowed the other, unstimulated, half of the dura to be used as a control. The ratio of the amount of extravasation in the dura from the stimulated side compared to the unstimulated side was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was estimated.

Figure 1:
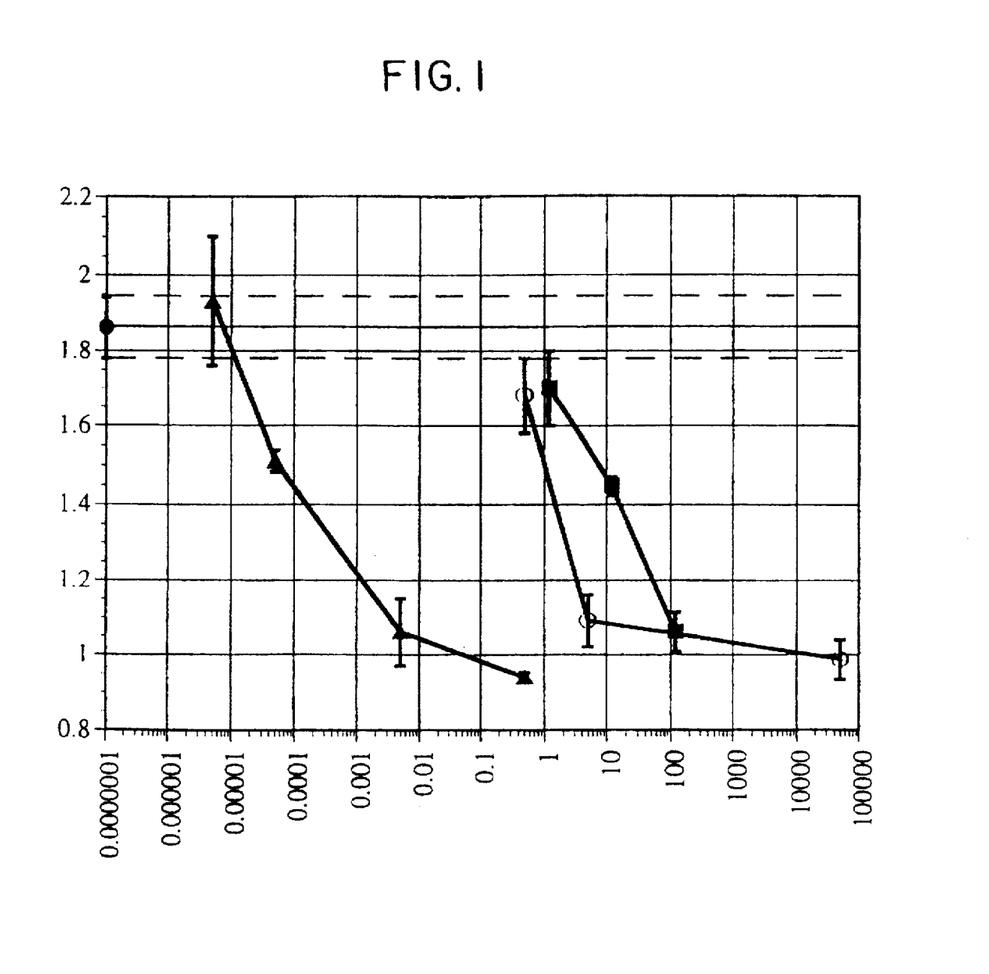

A typical such dose response curve is depicted in FIG. 1. These results demonstrate a marked advantage for the combination of the serotonin agonist with a tachykinin receptor antagonist over either therapeutic strategy alone. The converse of this experiment, that experiment in which the concentration of the tachykinin receptor antagonist is maintained at a conscant level and varying concentrations of the serotonin agonist is administered, showed very similar results.

The advantages of this synergistic combination therapy are obvious. Among its other advantages, this combination therapy greatly increases the therapeutic index of a composition in treating migraine. A markedly decreased amount of a seroconin agonist may now be administered to a patient, presumably greatly lessening the likelihood and severity of any adverse events. The reduced amount of active ingredient necessary for a therapeutic effect makes possible other routes of formulation than those currently employed. Rapid onset formulations such as buccal or sublingual may now be developed. Sustained release formulations are now more feasible due to the lower amounts of active ingredient necessary.

A comparison of the binding of serotonin agonists to the individual subtypes of receptors with the efficacy of a compound in the dural extravasation model of migraine demonstrates that the efficiency of binding to a subset of receptor subtypes is more predictive of efficacy in the migraine model. This analysis clearly demonstrates that the $5-HT_1$ series of receptors are those primarily involved in the modulation of migraine. Preferred receptor subtypes are the $5-HT_{1B}$, $5-HT_{1D}$, and $5-HT_{1F}$. It, therefore, follows that the preferred methods of the present invention are those methods employing a compound that has affinity for one of these receptor subtypes.

In comparing the protection of a serotonin agonist in the dural extravasation model of migraine with its binding strength to various serotonin receptors, it was seen that the efficiency of binding to the $5-HT_{1F}$ receptor subtype was directly predictive of its efficacy in protecting against migraine headache in the dural extravasation model. These results strongly suggest that the $5-HT_{1F}$ subtype of serotonin receptors is most directly linked to migraine and migraine alleviation. For that reason, the most preferred serotonin agonists employed in the methods of the present invention are those agonists having affinity for the $5-HT_{1F}$ receptor subtype.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
| --- | --- |
| Active Ingredient(s) | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/capsule) |
| --- | --- |
| Active Ingredient(s) | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
| --- | --- |
| Active Ingredient(s) | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/capsule) |
| --- | --- |
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
| --- | --- |
| Active Ingredient(s) | 40.0 mg |
| Starch | 109.0 mg |

-continued

| Ingredient | Quantity (mg/capsule) |
| --- | --- |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
| --- | --- |
| Active Ingredient(s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
| --- | --- |
| Active Ingredient(s) | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| Active Ingredient(s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| Active Ingredient(s) | 250.0 mg |
| Isotonic saline | 1000 ml |

Formulation Preparation 10

A topical formulation may be prepared as follows:

| Ingredient | Quantity |
| --- | --- |
| Active Ingredient(s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latenciation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

The administration of the serotonin agonist may be simultaneous with, before, or after the administration of the tachykinin receptor antagonist. If it is desired to administer the serotonin agonist simultaneously with the tachykinin receptor antagonist, the two active ingredients may be combined into one pharmaceutical formulation or two formulations may be administered to the patient.

Many factors will dictate the order of administration of the serotonin agonist and the tachykinin receptor antagonist. Some of these considerations include: the particular compounds employed; the manner in which each active ingredient is formulated; whether the administration is prophylactic or curative in nature; and the condition of the patient.

We claim:

1. A method for the treatment or prevention of migraine in a mammal which comprises administering to a mammal in need thereof the tachykinin receptor antagonist (R)-3-(1H-indol-3-yl)-1-|N-(2-methoxybenzyl)acetylano]-2-|N-(2-(4-(piperidin-1-yl)piperidin-1yl)acetyl)amino|propane and the serotonin agonist sumatriptan.

2. A method as claimed in claim 1 in which the mammal in need of treatment is administered a composition possessing both (R)-3-(1H-indol-3-yl)-1-[N-(2-methoxybenzyl)acetylamino|-2-|N-(2-(4-(piperidin-1-yl)piperidin-1-yl)acetyl)amino|propane and sumatriptan.

3. A method as claimed in claim 1 in which (R)-3-(1H-indol-3-yl)-1-|N-(2-melthoxybenzyl)acetylamino]-2-[N-(2-(4-(piperidin-1-yl)piperidin-1-yl)acetyl)amino|propane is administered prior to the administration of sumatriptan.

4. A method as claimed in claim 1 in which (R)-3-(1H-indol-3-yl)-1-[N-(2-methoxybenzyl)acetylamino]-2-[N-(2-(4-(piperidin-1-yl)piperidin-1-yl)acetyl)amino]propane is administered after the administration of sumatriptan.

5. A pharmaceutical formulation comprising (R)-3-(1H-indol-3-yl)-1-[N-(2-methoxybenzyl)acetylamino]-2-[N-(2-(4-(piperidin-1-yl)piperidin-1-yl)acetyl)amino]propane and sumatriptan in an amount that the aggregate has efficacy as an anti-migraine agent, in combination with one or more pharmaceutically acceptable excipients, carriers, or diluents therefor.

* * * * *